(12) United States Patent
Akihiro (10) Patent No.: US 12,357,492 B2
(45) Date of Patent: Jul. 15, 2025

(54) NASAL DILATOR

(71) Applicant: Shu-Chen Tsai, Taipei (TW)

(72) Inventor: Yoshiaki Akihiro, Taipei (TW)

(73) Assignee: Shu-Chen Tsai, Taipei (TW)

( * ) Notice: Subject to any disclaimer, the term of this patent is extended or adjusted under 35 U.S.C. 154(b) by 254 days.

(21) Appl. No.: 18/208,769

(22) Filed: Jun. 12, 2023

(65) Prior Publication Data

US 2023/0398015 A1    Dec. 14, 2023

(30) Foreign Application Priority Data

Jun. 14, 2022    (TW) .................................. 111122012

(51) Int. Cl.
*A61F 5/08*        (2006.01)
(52) U.S. Cl.
CPC ..................................... *A61F 5/08* (2013.01)

(58) Field of Classification Search
CPC ......... A61F 5/56; A61F 5/08; A61M 16/0666; A61M 2210/0618
See application file for complete search history.

(56) References Cited

U.S. PATENT DOCUMENTS

2020/0206012 A1*   7/2020   Akihiro ..................... A61F 5/08

* cited by examiner

*Primary Examiner* — Majid Jamialahmadi (57) ABSTRACT

A nasal dilator includes a right nasal inserter, a left nasal inserter and a connecting portion. The right nasal inserter has a cylindrical first body, with a first hollow portion inside the first body, and a plurality of first communication holes on the outer side of the first body to communicate with the outside air. The left nasal inserter has a cylindrical second body, with a second hollow portion inside the second body, and a plurality of second communication holes on the outer side of the second body to communicate with the outside air. The connecting portion is used to connect the first body and the second body, and connect through the outer edge of the bottom of the two.

12 Claims, 10 Drawing Sheets

NASAL DILATOR

BACKGROUND OF THE INVENTION

1. Field of the Invention

The present invention relates to a nasal inserter, especially a nasal dilator that can prevent falling off and avoid ugly appearance.

2. Description of the Related Art

The existing nasal inserter needs to expand the nasal cavity in order to deliver more air to the respiratory tract through the nasal cavity, so if the nasal dilator is enlarged, the nasal inserter will not be easily inserted into the nasal cavity. On the other hand, if the nasal inserter is made smaller, although the nasal inserter can be easily inserted into the nasal cavity, it cannot fully expand the nasal cavity, so more air cannot be delivered to the respiratory tract through the nasal cavity. In addition, the nasal inserter is also easy to fall out of the nasal cavity. Therefore, the existing nasal inserter has the problem that it cannot be easily inserted into the nasal cavity, transport more air through the nasal cavity, and prevent it from falling out of the nasal cavity at the same time.

In addition, the existing nasal inserter has a problem that when the nasal inserter is inserted into the nasal cavity, the nose expands to the left and right to form a so-called dumpling nose, which deteriorates the appearance of the face.

SUMMARY OF THE INVENTION

The invention provides a nasal dilator, comprising a right nasal inserter, a left nasal inserter and a connecting portion. The right nasal inserter comprises a cylindrical first body, with a first hollow portion inside the first body. The upper side of the first body has a first pressing portion. The end of the bottom and the end of the top of the first pressing portion in the extension direction are integrated with the first body. The first body has a first right opening at the bottom and a second right opening at the top. The left nasal inserter comprises a cylindrical second body, with a second hollow portion inside the second body. The upper side of the second body has a second pressing portion. The end of the bottom and the end of the top of the second pressing portion in the extension direction are integrated with the second body. The second body has a first left opening at the bottom and a second left opening at the top.

DETAILED DESCRIPTION OF THE PREFERRED EMBODIMENT

Please refer to FIGS. 1-7. As shown in the drawings, the nasal dilator 100 provided by the present invention is integrally formed of elastic synthetic resin, and the whole can be elastically deformed, and the synthetic resin constituting the nasal dilator 100 is, for example, styrene-based elastomer, polyester elastomer, silicone rubber, polyethylene or vinyl chloride. The nasal dilator 100 comprises a right nasal inserter 110, a left nasal inserter 120 and a connecting portion 130. The right nasal inserter 110 comprises a first body 111, which is cylindrical, and a first protruding portion 112 arranged on the outer edge of the bottom end of the first body 111. The first body 111 has a first hollow portion 113 inside, and the outer side of the first body 111 has a plurality of first communication holes 114 to communicate with the outside air. The first communication holes 114 are through holes that penetrate the first body 111 in the wall thickness direction, communicate the first hollow portion 113 with the outside, and the first communication holes 114 extend along the extension direction of the first hollow portion 113. The first communication holes 114 are formed on the outer wall of the first body 111, the outer wall referred to here is the side wall where the right nasal inserter 110 and the left nasal inserter 120 are not facing each other. The top of the first body 111 has a plurality of first guide portions 116 and there are gaps between the first guide portions 116, wherein the first guide portions 116 are in a semi-cylindrical shape, protruding from the inner wall forming the first hollow portion 113 at the end of the top end and extending upward. The first body 111 has a first right opening 117 at the bottom and a second right opening 118 at the top.

The left nasal inserter 120 comprises a second body 121, which is cylindrical, and a second protruding portion 122 arranged on the outer edge of the bottom end of the second body part 121. The second body 121 has a second hollow portion 123 inside, and the outer side of the second body 121 has a plurality of second communication holes 124 to communicate with the outside air. The second communication holes 124 are through holes that penetrate the second body 121 in the wall thickness direction, communicate the second hollow portion 123 with the outside, and the second communication holes 124 extend along the extension direction of the second hollow portion 123. The second communication holes 124 are formed on the outer wall of the second body 121, the outer wall referred to here is the side wall where the right nasal inserter 110 and the left nasal inserter 120 are not facing each other. The top of the second body 121 has a plurality of second guide portions 126 and there are gaps between the second guide portions 126, wherein the second guide portions 126 are in a semi-cylindrical shape, protruding from the inner wall forming the second hollow portion 123 at the end of the top end and extending upward. The second body 121 has a first left opening 127 at the bottom and a second left opening 128 at the top. The connecting portion 130 is used to connect the first body 111 and the second body 121, and is connected through the outer edge of the bottom of the two, that is to say, the connecting portion 130 is used to connect the right nasal inserter 110 and the left nasal inserter 120.

Specifically, the nasal dilator 100 has the following features in order to achieve the goal of not falling off while wearing it while sleeping. In line with the curved shape inside the nasal cavity, the inserters of nasal dilator 100 are not linear, but are divided into front and rear bodies. At the entrance of the nasal cavity there is a recess called the nasal vestibule. When the nasal dilator 100 is inserted into the nasal cavities, the first enlarged diameter part 119 and the second enlarged diameter part 129 at the end of the bottom end of the nasal dilator 100 will fit into the recesses to prevent falling off. In addition, in order to increase the flow rate of air inhaled into the nasal cavities, the bottom of the first enlarged diameter part 119 and the bottom of the second enlarged diameter part 129 embedded in the nasal vestibules form a platform, which can prevent the inhaled air from turbulent flow. The entrance of the nasal cavities will be raised to form a flat shape due to the embedding of the first enlarged diameter part 119 and the second enlarged diameter part 129, so that the inflow of air can be smooth and more air can be inhaled because of the widening of the nasal cavity entrance. Furthermore, in order to allow the airflow flowing into the nasal cavities to reach the superior meatus or the middle meatus, there are several curved plates or tubes at the end of the top side facing the upper guiding portions. When the rapid airflow enters the superior meatus and middle meatus through the front of the natural orifice of the paranasal sinus, it will cause the air pressure in the paranasal sinus to change, causing the microvessels in the paranasal sinus to release nitric oxide (NO). The nasal dilator 100 further comprises a first pressing portion 1195 and a second pressing portion 1295 disposed on the first body 111 and the second body 121 and extending from the bottom end side to the top end side. When pushing the bridge of the nose upwards from the top of the nasal cavity, the position of the nasal muscles will be moved upwards and the facial muscles above it will also be pushed to form a series of stretching movements.

Further, the bottom outer edge of the first body 111 is provided with the first enlarged diameter part 119, and the first protruding portion 112 extends from one side of the first enlarged diameter part 119. At least one end of the first enlarged diameter part 119 has a first thin-walled portion 1191, and when stress is concentrated on the first thin-walled portion 1191 of the first enlarged diameter part 119, the first thin-walled portion 1191 will be squeezed and deformed, the bottom outer edge of the second body 121 is provided with the second enlarged diameter part 129, and the second protruding portion 122 extends from one side of the second enlarged diameter part 129. At least one end of the second enlarged diameter part 129 has a second thin-walled portion 1291, and when stress is concentrated on the second thin-walled portion 1291 of the second enlarged diameter part 129, the second thin-walled portion 1291 will be squeezed and deformed. It is worth mentioning that there is an arc-shaped hole 119A at the triangular tip of the first enlarged diameter part 119, and its function is to match the height of the user's nose so that it can be stretched without being affected by the height of the nose. Similarly, there is also an arc-shaped hole 129A at the triangular tip of the second enlarged diameter part 129.

In addition, the upper side of the first body 111 is provided with the first pressing portion 1195, and the bottom end and the top end of the first pressing portion 1195 in the extending direction are integrated with the first body 111, the upper side of the second body 121 is provided with the second pressing portion 1295, and the bottom end and the top end of the second pressing portion 1295 in the extending direction are integrated with the second body 121.

It is worth mentioning that the right nasal inserter 110 further has a first expansion portion 115, which is used to expand the volume of the right nasal cavity, and the first expansion portion 115 is arranged next to the first pressing portion 1195 of the first body 111. The first expansion portion 115 is circular and protrudes outward from the inner and lower side walls of the first body 111. The inner side wall referred to here refers to the side walls where the right nasal inserter 110 and the left nasal inserter 120 face each other. In addition, the left nasal inserter 120 further has a second expansion portion 125, which is used to expand the volume of the left nasal cavity, and the second expansion portion 125 is arranged next to the second pressing portion 1295 of the second body 121. The second expansion portion 125 is circular and protrudes outward from the inner and lower side walls of the second body 121. The inner side wall referred to here refers to the side walls where the right nasal inserter 110 and the left nasal inserter 120 face each other.

When inserting the nasal dilator 100 into the right and left nasal cavities, first insert the first body 111 and the second body 121 into the right and left nasal cavities respectively. At this time, insert the nasal dilator 100 into the right and left nasal cavities, and the first pressing portion 1195 and the second pressing portion 1295 will simultaneously lean against the inner wall of the right and left nasal cavities to press the inner walls of the right and left nasal cavities to expand the right and left nasal cavities while inserting it into the right and left nasal cavities. When the nasal dilator 100 is further inserted into the right and left nasal cavities, the first enlarged diameter part 119 and the second enlarged diameter part 129 will also be inserted into the right and left nasal cavities. At this time, the stress is concentrated on the first thin-walled portion 1191 of the first enlarged diameter part 119 and the second thin-walled portion 1291 of the second enlarged diameter part 129. This will make the first thin-walled portion 1191 and the second thin-walled portion 1291 elastically deformed, so the first enlarged diameter part 119 and the second enlarged diameter part 129 can be easily inserted into the right and left nasal cavities regardless of the shape of the right and left nasal cavities.

Next, in the state where the first enlarged diameter part 119 is inserted into the nasal cavity, the first enlarged diameter part 119 engages with the nasal vestibule in the nasal cavity, which can definitely inhibit the nasal dilator 100 from falling out of the nasal cavity. When the nasal dilator 100 is inserted into the right and left nasal cavities, the first pressing portion 1195 and the second pressing portion 1295 will press the bridge of the nose outward, so it can restrain the nose from expanding to the left and right, and avoid turning into a dumpling nose and making the face look ugly. Furthermore, when the first pressing portion 1195 and the second pressing portion 1295 press the inner walls of the right and left nasal cavities upward, the reaction force received from the inner walls is transmitted to the first protruding portion 112 and the second protruding portion 122, and the first protruding portion 112 and the second protruding portion 122 will press the depressor septi nasi muscle, thereby widening the nasal entrance. In addition, by connecting the first hollow portion 113 with the external first communication holes 114 and connecting the second hollow portion 123 with the external second communication holes 124, the air in the first communication holes 114 and the second communication holes 124 is sucked into the first hollow portion 113 and the second hollow portion 123 respectively by the airflow in the first hollow portion 113 and the second hollow portion 123. Compared with the first hollow portion 113, the nasal cavity and the first communication holes 114 will become negative pressure, so that the body fluid secreted by the nasal mucosa in the nasal cavity can easily evaporate into the first hollow portion 113 through the first communication holes 114. Then, the body fluid evaporated to the first hollow portion 113 reaches the deep nasal cavity or the mucous membrane tissue of the pharynx along with the airflow in the first hollow portion 113. As a result, the deep nasal cavity or pharyngeal mucous membrane tissue can be kept moist, and the function of the deep nasal cavity or pharyngeal mucous membrane tissue can be protected.

Furthermore, pressing the depressor septi nasi muscle through the first expansion portion 115 and the second expansion portion 125 can expand the volume of the nasal cavity, so more external air can be inhaled through the nasal cavity, and more exhaled air can be discharged through the nasal cavity.

The first hollow portion 113 of the nasal dilator 100 extends upward from the end on the bottom end side, and the first guide portions 116 extend upward from the end on the top end side, so that the outside air is sucked into the first hollow portion 113 through the first right opening 117 of the nasal dilator 100, and the air is guided upward through the first hollow portion 113 and first guide portions 116, and then discharged from the second right opening 118 and taken into the body. Afterwards, the air expelled by the second right opening 118 is directed into the superior or middle nasal meatus. The above is explained with the right nasal inserter 110, and the same is true for the left nasal inserter 120, which will not be repeated here. Here, the nasal cavity is divided into superior nasal meatus, middle nasal meatus and inferior nasal meatus from the top by the turbinates protruding from the left and right side walls. When the fast-flowing air enters the superior nasal meatus and middle nasal meatus, the load generated by the fast-flowing air stimulates the activation of nitric oxide (NO) synthetic enzyme (NOS) to produce nitric oxide. Nitric oxide has bactericidal effect and the effect of relaxing smooth muscle and dilating blood vessels. Therefore, the air released from the second right opening 118 and guided to the superior nasal meatus or middle nasal meatus stimulates the superior nasal meatus and middle nasal meatus to produce nitric oxide, which can improve the bactericidal effect on viruses and expand blood vessels to lower blood pressure, thereby inhibiting myocardial infarction.

Figure 1:
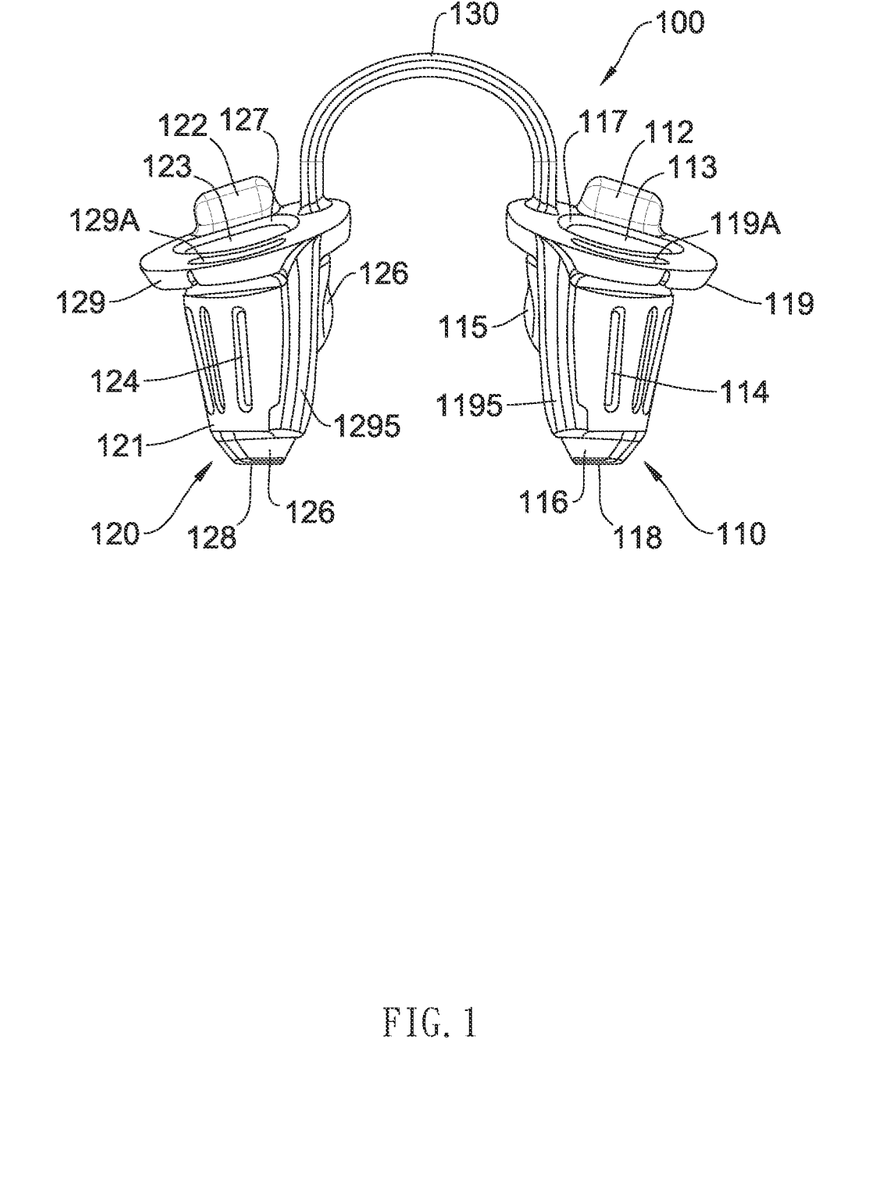
FIG. 1 is a schematic diagram of the nasal dilator of the present invention.
Figure 2:
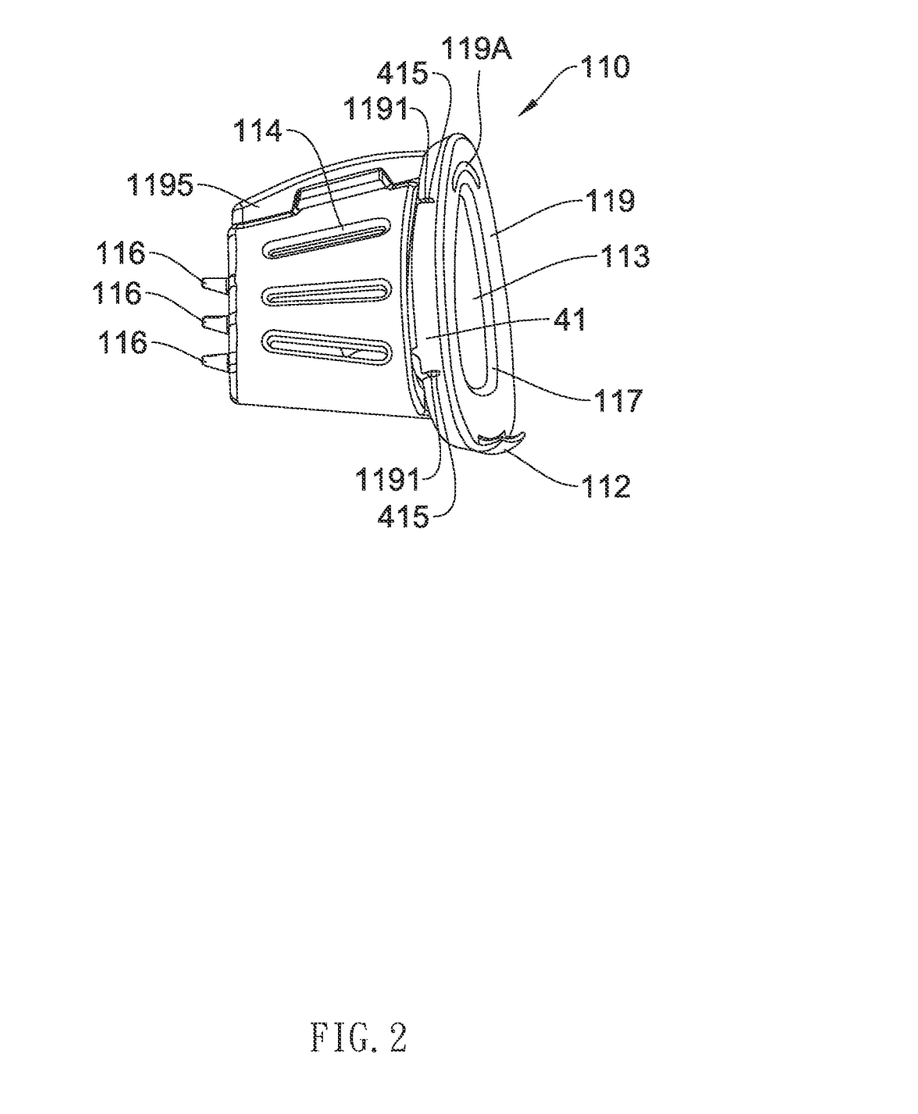
FIG. 2 is the right side view of the right nasal inserter of the nasal dilator of the present invention.
Figure 3:
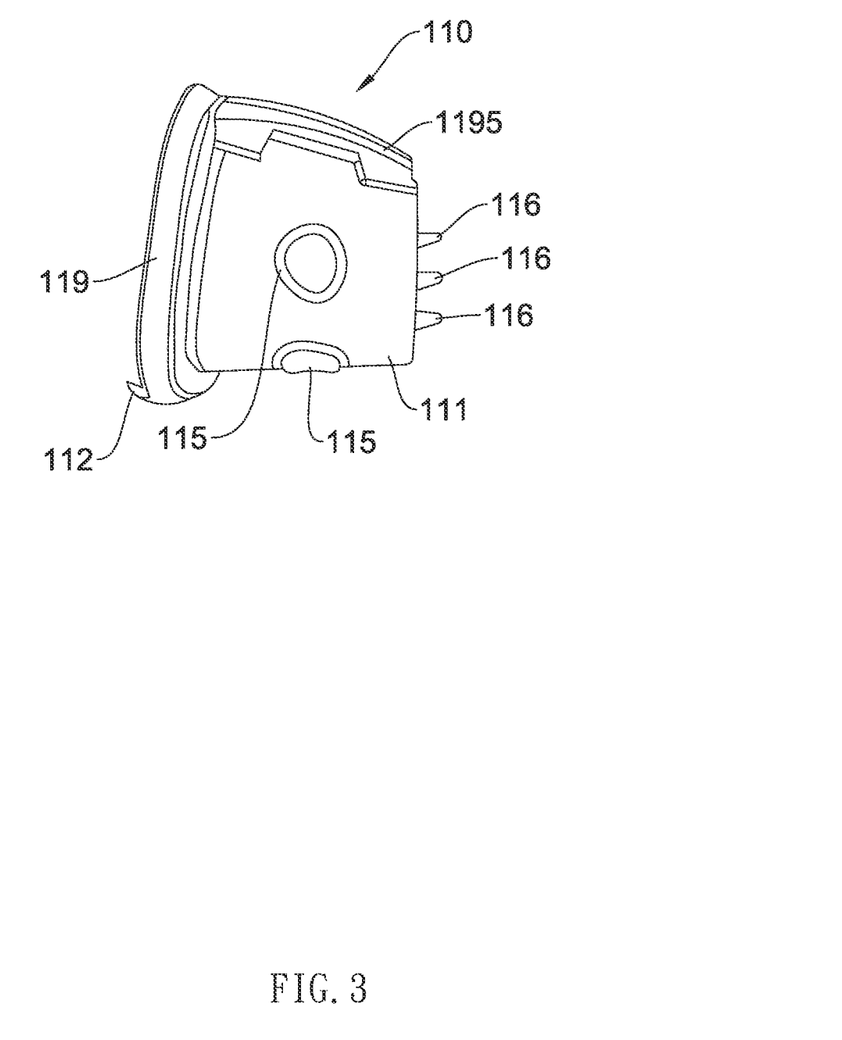
FIG. 3 is the left side view of the right nasal inserter of the nasal dilator of the present invention.
Figure 4:
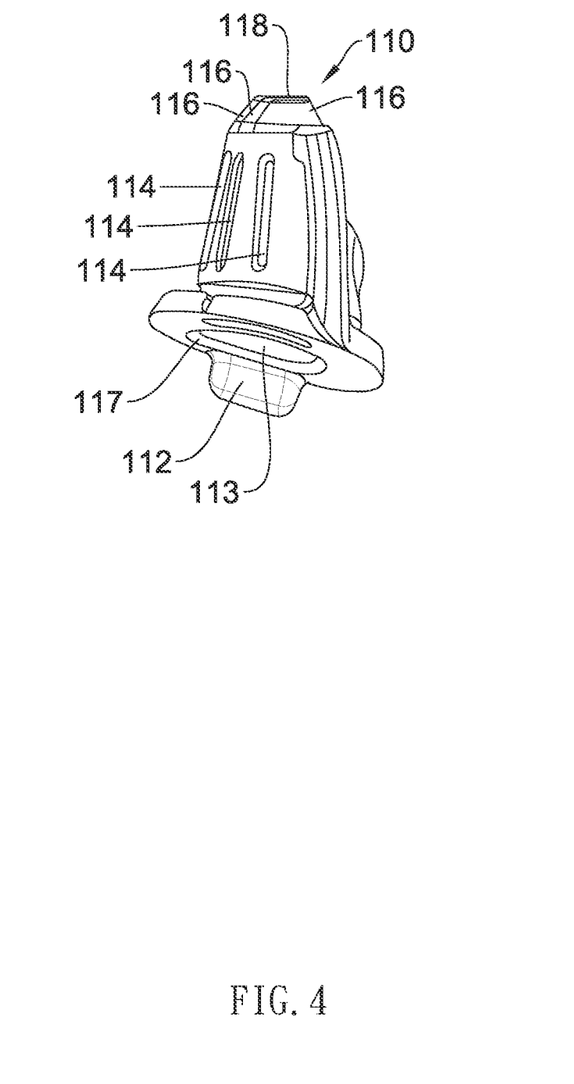
FIG. 4 is a schematic plan view of the right nasal inserter of the nasal dilator of the present invention.
Figure 5:
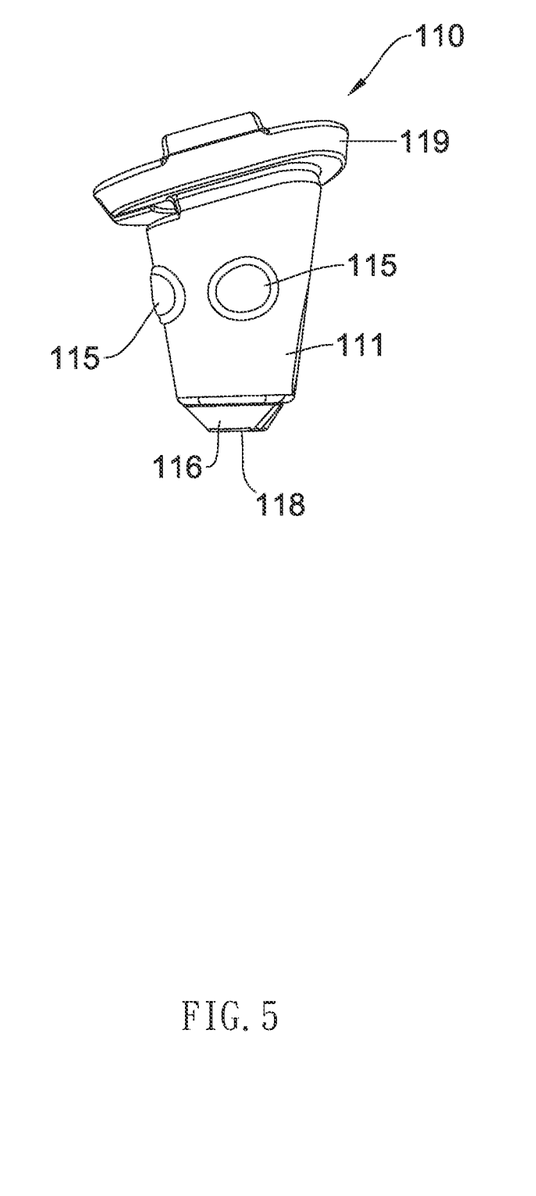
FIG. 5 is a bottom view of the right nasal inserter of the nasal dilator of the present invention.
Figure 6:
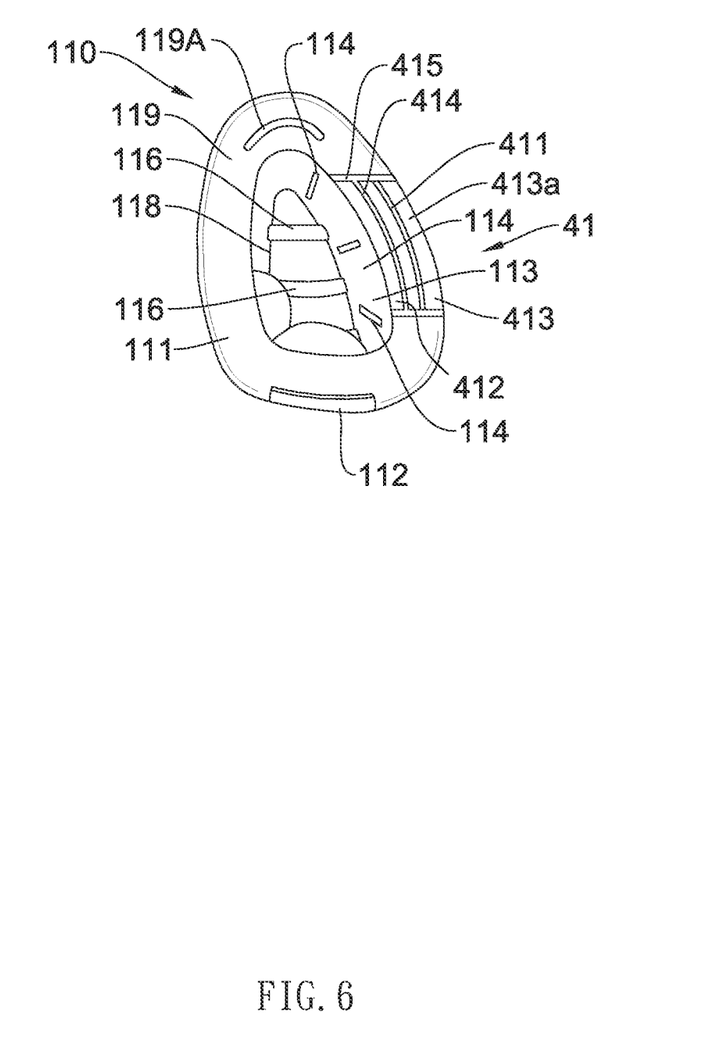
FIG. 6 is the rear view of the right nasal inserter of the nasal dilator of the present invention.
Figure 7:
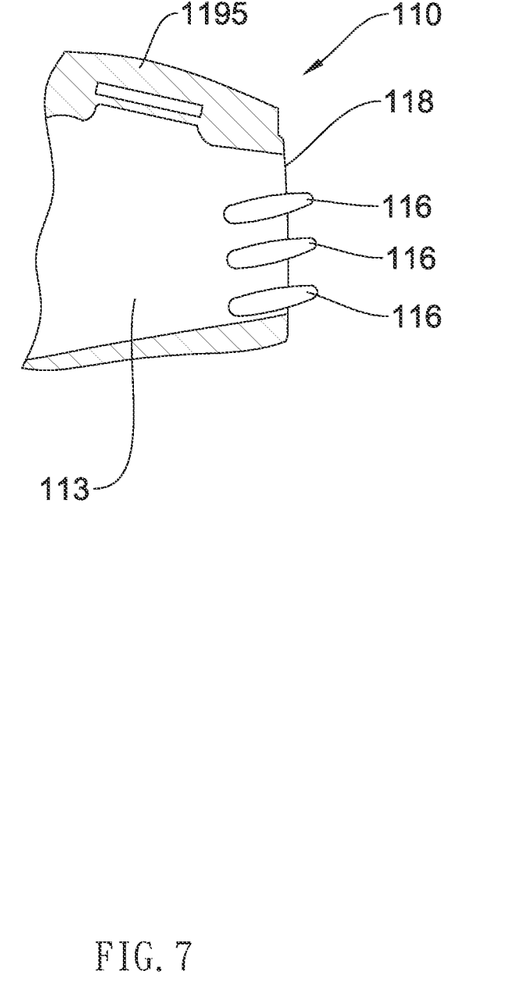
FIG. 7 is a sectional view of the right nasal inserter of the nasal dilator of the present invention.
Figure 8:
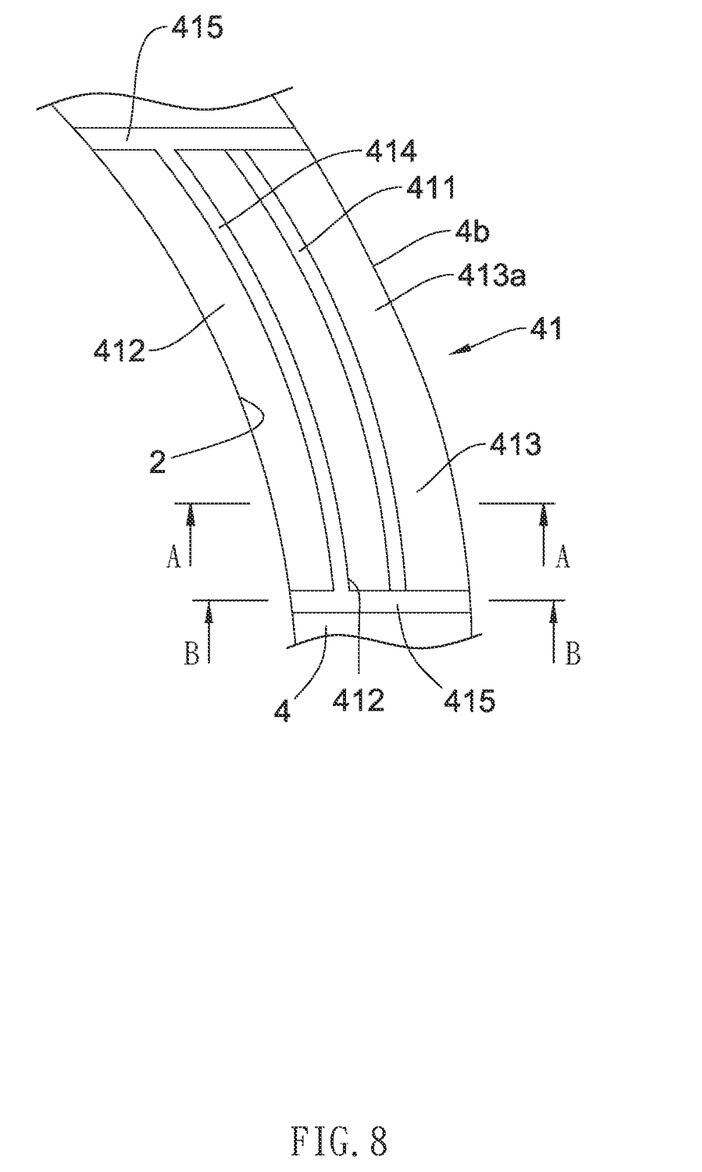
FIG. 8 is a partially enlarged schematic diagram of the nasal dilator of the present invention.
Figure 9:
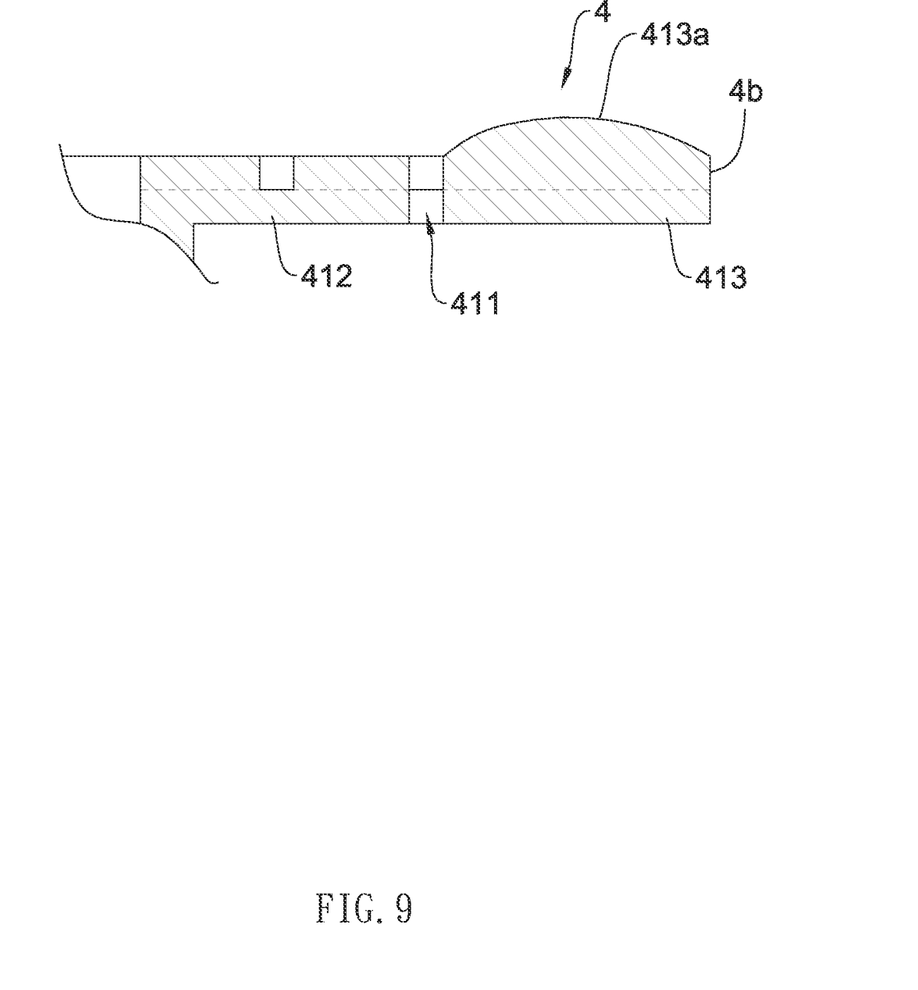
FIG. 9 is the A-A sectional view of FIG. 8 of the present invention.
Figure 10:
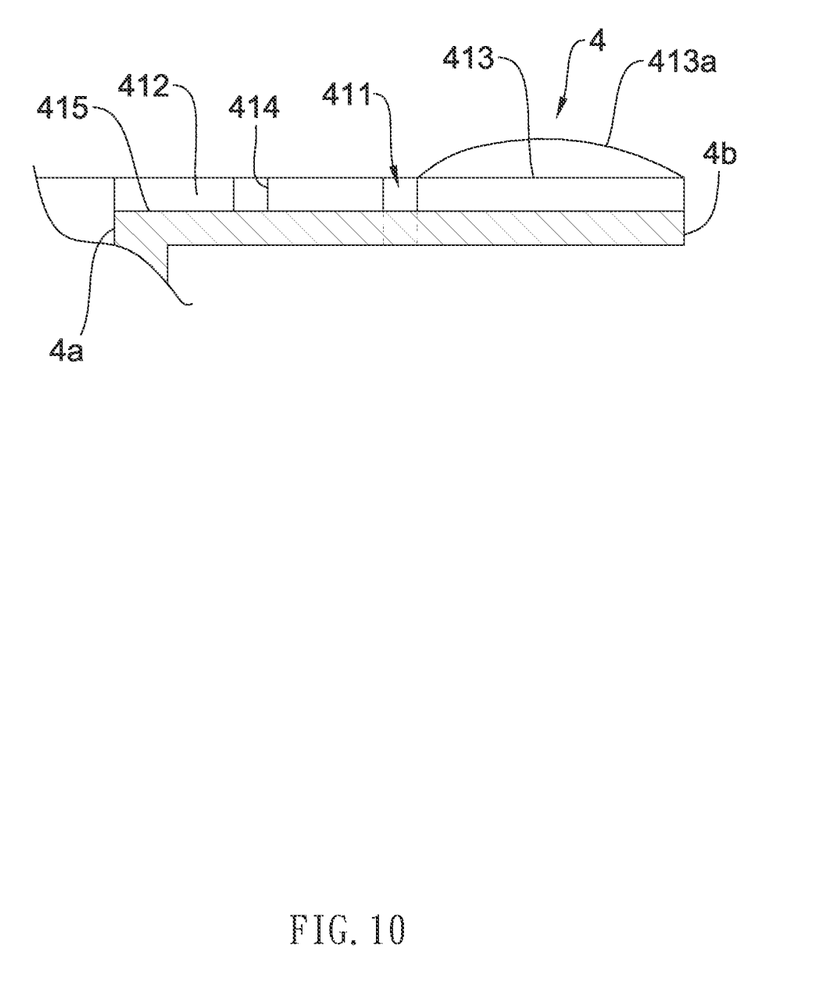
FIG. 10 is the B-B sectional view of FIG. 8 of the present invention.

In addition, please refer to FIG. 1, FIG. 8 to FIG. 10 at the same time, where FIG. 8 is a partially enlarged schematic diagram of the nasal dilator of the present invention, FIG. 9 is the A-A sectional view of FIG. 8 of the present invention, and FIG. 10 is the present invention B-B sectional view of FIG. 8. As shown in FIG. 6 and FIG. 8, the first enlarged diameter part 119 and the second enlarged diameter part 129 respectively comprise an outer portion 41, a slit portion 411, an inner portion 412, an edge portion 413, a first concave groove 414 and second concave grooves 415. The slit portion 411 is set between a pair of second concave grooves 415. The outer portion 41 has a first concave groove 414 arranged between the slit portion 411 and the first right opening 117 (the first left opening 127 is the same) along the slit portion 411. In addition, the outer portion 41 is arranged along the protruding direction of the first enlarged diameter part 119 (the same is true for the second enlarged diameter part 129) and a corresponding pair of second concave grooves 415 is arranged at a predetermined interval.

In the nasal cavity insertion tool for the above operation, a slit portion 411 is provided between a pair of second concave grooves 415, and the slit portion 411 adjusts and absorbs (receives) pressure from the inner wall of the nasal cavity according to the distance between a pair of second concave grooves 415. It is worth mentioning that the second concave grooves 415 in the present invention can adjust and absorb pressure. Further, when the nasal dilator 100 is kept in the nasal cavity and the first hollow portion 113 (the second hollow portion 123 is the same) is located in the center of the nasal cavity, more air can be sucked into the body from the outside through the first hollow portion 113 (the second hollow portion 123 is the same). The slit portion 411 of the nasal dilator 100 can absorb the elastic deformation caused by the inner wall of the alar side squeezing the outer portion 41, and prevent the first hollow portion 113 (the second hollow portion 123 is the same) from moving from the center of the nasal cavity to the side of the nasal septum. In addition, even if the pressure on the inner wall of the nasal cavity on the alar side cannot be completely absorbed by the slit portion 411, it will be absorbed by the first concave groove 414 to ensure that the first hollow portion 113 (the second hollow portion 123 is the same) will not move from the center of the nasal cavity to the side of the nasal septum nasal side. As a result, the nasal dilator 100 can keep the hollow portion 31 in the center of the nasal cavity, and inhale more air from the outside into the body through the first hollow portion 113 (the same applies to the second hollow portion 123).

Since the first body 111 and the first enlarged diameter part 119 are arranged around the first right opening 117, and the second body 121 and the second enlarged diameter part 129 are arranged around the first left opening 127, when the nasal dilator 100 is inserted into the right and left nasal cavities, in the direction of the outer portions 41 of the first right opening 117 and first left opening 127, it can prevent falling out of the right and left nasal cavities without increasing the overall size. In addition to maintaining the proper position in the right and left nasal cavities, it can also force more air through the right and left nasal cavities into the respiratory tract.

In the above embodiment, the second concave grooves 415 are arranged from the end 4a to the end 4b along the protruding direction of the first enlarged diameter part 119 (the same is true for the second enlarged diameter part 129). The second concave grooves 415 can be placed in the intersection with the slit portion 411.

In the above embodiment, a convex shape is set at the edge portion 413 toward the first right opening 117 (that is, the edge portion 413 is convex toward one end side), and at the first enlarged diameter part 119 (the second enlarged diameter part 129 is the same). In addition, a curved surface 413a is formed at the central part in the protruding direction of the first enlarged diameter part 119 (the second enlarged diameter part 129 is the same) so that the thickness becomes thinner toward the end 4b. In addition, a curved surface may be formed such that the thickness becomes thinner from the edge portion 413 on the slit portion 411 side toward the end 4b.

In summary, the nasal dilator disclosed in the present invention can bring the following effects:
1. It can prevent from falling out of the nasal cavity as much as possible;
2. It can increase the flow rate of air inhaled into the nasal cavity; and
3. It can suppress the ugly appearance of the face when it is inserted into the nasal cavity.

What is claimed is:

1. A nasal dilator, comprising:

a right nasal inserter, said right nasal inserter comprising a first body, which is cylindrical, a first hollow portion located inside said first body, a first pressing portion located on an upper side of said first body, a first right opening located on the bottom of said first body and a second right opening located on the top of said first body, said first pressing portion having bottom end and top end thereof in the extending direction integrated with said first body;

a left nasal inserter, said left nasal inserter comprising a second body, which is cylindrical, a second hollow portion located inside said second body, a second pressing portion located on an upper side of said second body, a first left opening located on the bottom of said second body and a second left opening located on the top of said second body, said second pressing portion having bottom end and top end thereof in the extending direction integrated with said second body;

wherein said right nasal inserter further comprises a first enlarged diameter part located on an outer edge of the bottom of said first body and said left nasal inserter further comprises a second enlarged diameter part located on an outer edge of the bottom of said second body, said first enlarged diameter part and said second enlarged diameter part each comprise an outer portion, a slit portion, an inner portion, an edge portion, a first concave groove and a pair of second concave grooves, and said slit portion of each of said first and second enlarged diameter parts is set between said pair of second concave grooves of their respective first and second enlarged diameter parts; and wherein said first concave groove of each of said first and second enlarged diameter parts extends from one second concave groove of said pair of second concave grooves to another second concave groove of said pair of second concave grooves of their respective first and second enlarged diameter parts.

2. The nasal dilator as claimed in claim 1, wherein said first enlarged diameter part comprises a first thin-walled portion located on at least one end thereof, and when stress is concentrated on said first thin-walled portion of said first enlarged diameter part, said first thin-walled portion is squeezed and deformed.

3. The nasal dilator as claimed in claim 1, wherein said second enlarged diameter part comprises a second thin-walled portion located on at least one end thereof, and when stress is concentrated on said second thin-walled portion of said second enlarged diameter part, said second thin-walled portion is squeezed and deformed.

4. The nasal dilator as claimed in claim 1, wherein said right nasal inserter further comprises a plurality of first communication holes located on an outer side of said first body to communicate with the outside air, and a plurality of first guide portions located on the top of said first body with gaps arranged between said first guide portions.

5. The nasal dilator as claimed in claim 1, wherein said left nasal inserter further comprises a plurality of second communication holes located on an outer side of said second body to communicate with the outside air, and a plurality of second guide portions located on the top of said second body with gaps arranged between said second guide portions.

6. The nasal dilator as claimed in claim 1, wherein said right nasal inserter further comprises a first protruding portion located on the outer edge of the bottom of said first body, said first protruding portion extending from one side of said first enlarged diameter part.

7. The nasal dilator as claimed in claim 1, wherein said left nasal inserter further comprises a second protruding portion located on the outer edge of the bottom of said second body, said second protruding portion extending from one side of said second enlarged diameter part.

8. The nasal dilator as claimed in claim 1, further comprising a connecting portion used to connect said first body and said second body, and connect through a bottom outer edge of said first body and a bottom outer edge of said second body.

9. The nasal dilator as claimed in claim 1, wherein said outer portion of said first or second enlarged diameter parts has said first concave groove disposed along said slit portion between said slit portion and said first right or left openings, said outer portion of said first or second enlarged diameter parts is arranged along the protruding direction of said first enlarged diameter part or said second enlarged diameter part, and the corresponding pair of said second concave grooves of said first or second enlarged diameter parts are arranged at a predetermined interval.

10. The nasal dilator as claimed in claim 1, wherein said edge portion of said first or second enlarged diameter parts is convex toward one end side, and a curved surface is formed at the center of the protrusion direction of said first enlarged diameter part or said second enlarged diameter part so that the thickness becomes thinner toward the end.

11. The nasal dilator as claimed in claim 1, wherein said second concave grooves of said first or second enlarged diameter parts are used to regulate and absorb pressure.

12. The nasal dilator as claimed in claim 1, wherein said slit portion of said first or second enlarged diameter parts is used to absorb the elastic deformation caused by the inner wall of the alar side squeezing said outer portion.

* * * * *